(12) United States Patent
Brothers

(10) Patent No.: US 10,780,229 B2
(45) Date of Patent: Sep. 22, 2020

(54) LOW WASTE SYRINGE AND NEEDLE ASSEMBLAGE

(71) Applicant: David B. Brothers, Atlanta, GA (US)

(72) Inventor: David B. Brothers, Atlanta, GA (US)

(*) Notice: Subject to any disclaimer, the term of this patent is extended or adjusted under 35 U.S.C. 154(b) by 1076 days.

(21) Appl. No.: 14/847,825

(22) Filed: Sep. 8, 2015

(65) Prior Publication Data

US 2016/0008545 A1   Jan. 14, 2016

Related U.S. Application Data

(63) Continuation-in-part of application No. PCT/US2014/021937, filed on Mar. 7, 2014, and a
(Continued)

(51) Int. Cl.
*A61M 5/31* (2006.01)
*A61M 5/34* (2006.01)
(Continued)

(52) U.S. Cl.
CPC ........ *A61M 5/3134* (2013.01); *A61M 5/3129* (2013.01); *A61M 5/31513* (2013.01);
(Continued)

(58) Field of Classification Search
CPC .... A61M 5/3293; A61M 5/347; A61M 5/345; A61M 5/3134; A61M 2005/31516;
(Continued)

(56) References Cited

U.S. PATENT DOCUMENTS 5,085,638 A   2/1992   Farbstein et al.
6,010,486 A   1/2000   Carter
(Continued)

FOREIGN PATENT DOCUMENTS

CN   1293070   5/2001
CN   1294524   5/2001
(Continued)

OTHER PUBLICATIONS

Brothers, David B.; Extended European Search Report for serial No. 14760549.7, filed Mar. 7, 2014, dated Oct. 25, 2016, 7 pgs.
(Continued)

*Primary Examiner* — Rebecca E Eisenberg
*Assistant Examiner* — Weng Lee
(74) *Attorney, Agent, or Firm* — Womble Bond Dickinson (US) LLP

(57) ABSTRACT

A low-waste needle and syringe assembly for injecting a fluid into a patient is provided. The syringe has hatch marks printed on the outer wall of the body to indicate the amount of fluid and/or the concentration of the fluid contained in a fluid chamber of the syringe. A syringe tip defining a substantially frusto-conical interior void extends from an end wall of the syringe. A needle hub holds a needle and is configured so that the hub can be selectively and securely attached to the syringe. A frusto-conical member of the needle hub matingly engages the frusto-conical void of the syringe tip when the hub is secured to the syringe, forming a fluid-tight seal. A plunger positioned in the fluid chamber can be depressed by a user, and a piston cap attached to the plunger urges fluid in the chamber out of the chamber through the syringe tip and into the needle. The piston cap matingly engages the end wall of the syringe so that substantially all fluid is urged from the chamber to the needle.

27 Claims, 21 Drawing Sheets

Related U.S. Application Data continuation-in-part of application No. PCT/US2015/038448, filed on Jun. 30, 2015.

(60) Provisional application No. 61/774,297, filed on Mar. 7, 2013, provisional application No. 62/063,763, filed on Oct. 14, 2014, provisional application No. 62/019,072, filed on Jun. 30, 2014.

(51) Int. Cl.
*A61M 5/32* (2006.01)
*A61M 5/315* (2006.01)

(52) U.S. Cl.
CPC .......... *A61M 5/3202* (2013.01); *A61M 5/347* (2013.01); *A61M 2005/3126* (2013.01); *A61M 2005/31516* (2013.01); *A61M 2205/6081* (2013.01)

(58) Field of Classification Search
CPC ...... A61M 5/348; A61M 5/346; A61M 5/344; A61M 5/34; A61M 5/349
See application file for complete search history.

(56) References Cited

U.S. PATENT DOCUMENTS

| | | | |
|---|---|---|---|
| 6,132,416 | A | 10/2000 | Broselow |
| 2001/0053886 | A1 | 12/2001 | Caizza |
| 2003/0018301 | A1 | 1/2003 | Sheppard |
| 2003/0040720 | A1* | 2/2003 | Steube ............... A61M 5/34 604/240 |
| 2007/0235641 | A1 | 10/2007 | Allberg |
| 2007/0239115 | A1 | 10/2007 | Cecchi |
| 2008/0249480 | A1 | 10/2008 | Riesenberger et al. |
| 2008/0262435 | A1* | 10/2008 | Erickson ........... A61M 5/31531 604/192 |
| 2008/0269697 | A1 | 10/2008 | Bush et al. |
| 2010/0130961 | A1 | 5/2010 | Tucker |

FOREIGN PATENT DOCUMENTS

| | | |
|---|---|---|
| CN | 1758929 | 4/2006 |
| EP | 1406547 | 6/2010 |
| JP | 60-184548 | 9/1985 |
| JP | 60-184548 | 12/1985 |
| JP | S60-184548 | 12/1985 |
| JP | 2011136151 | 7/2011 |
| WO | 2012048324 | 4/2012 |
| WO | 2014138634 | 9/2014 |
| WO | 2016003981 | 1/2016 |

OTHER PUBLICATIONS

Brothers, David A.; International Preliminary Report and Written Opinion for Serial No. PCT/US15/38448, filed Jun. 30, 2015, dated Jan. 12, 2017, 9 pgs.

Brothers, David A.; International Search Report and Written Opinion for serial No. PCT/US15/38448, filed Jun. 30, 2015, dated Oct. 6, 2015, 11 pgs.

Brothers, David A.; U.S. Patent Application entitled: Low Waste Syringe and Needle Assemblage, having U.S. Appl. No. 62/019,072, filed Jun. 30, 2014, 41 pgs.

Brothers, David A.; U.S. Patent Application entitled: Low Waste Syringe and Needle Assemblage, having U.S. Appl. No. 62/063,763, filed Oct. 14, 2014, 44 pgs.

Brothers, David B., Internationai Preliminary Report on Patentability for serial No. PCT/US14/21937, filed Mar. 7, 2014, dated Sep. 8, 2015, 10 pgs.

Brothers, David B., International Search Report and Written Opinion for serial No. PCT/US14/21937, filed Mar. 7, 2014, dated Jul. 10, 2014, 14 pgs.

Brothers, David B., PCT Application entitled: Low Waste Syringe and Needle Assemblage having serial No. PCT/US2014/021937, filed May 10, 2014, 37 pgs.

Brothers, David B.; U.S. Provisional Application entitled: Low Waste Syringe and Needle Assemblage, having U.S. Appl. No. 61/774,297, filed Mar. 7, 2013, 35 pgs.

Notice of Allowance dated Dec. 245, 2018 from co-pending Canadian patent application No. 2,908,822.

* cited by examiner

LOW WASTE SYRINGE AND NEEDLE ASSEMBLAGE

CROSS-REFERENCE TO RELATED PATENT APPLICATION

This application is a continuation-in-part of PCT/US2014/021937, filed Mar. 7, 2014, which claims priority to U.S. Provisional Application No. 61/744,297, filed Mar. 7, 2013, and is a continuation-in-part of PCT/US2015/038448, filed Jun. 30, 2015, which claims priority to U.S. Provisional Application No. 62/063,763, filed Oct. 14, 2014, and U.S. Provisional Application No. 62/019,072, filed Jun. 30, 2014. The contents of each of the above-referenced patent applications and patents are hereby incorporated by reference in their entirety.

FIELD OF THE INVENTION

The field of this invention relates generally to needles and syringes for injecting a selected fluid into a patient, and more particularly to a low-waste syringe with at least one interchangeable needle. With more particularity, to a low-waste syringe with at least one interchangeable needle for injection of a desired neurotoxin therein a patient.

BACKGROUND

Neurotoxins such as Allergan's Botox® (Onabotulinumtoxin Type A), Medicis' Dysport® (Abobotulinumtoxin Type A) and Merz's Xeomin® (Incobotulinumtoxin Type A) have entered the medical aesthetic marketplace over the last 10-15 years and are currently used worldwide culminating in a global multi-billion dollar industry.

Neurotoxins are currently used for both medical and aesthetic purposes. The U.S. Food and Drug Administration (FDA) has approved Botox® for glabellar wrinkle reduction, Dysport® for cervical dystonia and glabellar creases and Xeomin® for cervical dystonia, blepharospasm and glabellar frown lines. Although these three drugs have FDA approval in the United States for "on label" use of their neurotoxin type A for the treatment of glabellar crease lines only, all three are used by most physician and nurse injectors "off label" for dynamic wrinkle reduction throughout the head and neck region.

The predominant company in the global aesthetic marketplace is Allergan which manufactures and distributes Botox® and Botox® Cosmetic globally (referred to hereinafter together as Botox®). Botox® is dispensed in 50 unit and 100 unit freeze dried vials and has to be reconstituted by the physician and/or nurse injectors (the "user") with preservative free, sterile injectable saline or the less painful, neutral pH bacteriostatic saline just before use. As one skilled in the art will appreciate, conventional neurotoxin vials are both multi and single dose and have an elastomeric top that can be pierced sterilely with a needle. Dysport® is dispensed in 300 unit vials and Xeomin® is dispensed in 100 unit vials similar to Botox®.

According to the FDA approval for Botox® and the package insert, the 100 unit vial should be reconstituted with 2.5 ml of 0.9% sterile, unpreserved saline. Most users, however, use bacteriostatic saline for the diminished discomfort and longer shelf-life it offers. Since its FDA approval, the clinical use of Botox® and the amount of diluent used for reconstitution has greatly evolved with most users and there is currently no standard dilution. The trend, however, has been toward lesser diluent volumes and more concentrated neurotoxin solutions. For example, the most common diluent volumes used today are 1 ml per vial (10 units/0.1 ml), 2 ml per vial (5 units/0.1 ml), 2.5 ml per vial (on-label for Botox® at 4 units/0.1 ml) and 4 ml per vial (2.5 units/0.1 ml). The reason for this trend is better placement control, better potential site efficacy at higher concentrations, less fluid volume injected with less pain and swelling and less chance of neurotoxin diffusion from the site of injection causing an adverse effect such as ptosis (drooping) of the upper eyelid or ptosis of the brow and eyebrow. There is no standard neurotoxin dilution for Botox® (other than the FDA approved 2.5 ml) and no standard delivery system based upon the practitioner's chosen amount of diluent and concentration of neurotoxin.

The average patient receiving Botox® for the treatment of dynamic glabellar frown lines will receive approximately 25 units of neurotoxin distributed over approximately 7 injections. Additional areas to be injected will require more neurotoxin and more injections. Each injection delivers approximately 1-4 units per injection depending upon the site and injector. If the neurotoxin is diluted with 1 ml of diluent this will produce a concentration of 10 units/0.1 ml or 1 unit/0.01 ml. In the above example in which a patient receives 25 units, a total volume of 0.25 ml will be injected into the patient. A conventional 1 ml syringe can be too large to accurately dispense these small volumes and the gradations on the syringe can be too difficult to read therefore not allowing for accurate dispensing of the neurotoxin. Additionally, 1 ml syringes are graduated in 1 ml increments and not units.

Additionally, most 1 ml neurotoxin syringes are not low-waste syringes, and a significant amount of neurotoxin can be wasted with each use of a multi-use vial. With each use of a syringe, costly neurotoxin will be lost in dead spaces of the syringe tip, the hub of the needle and/or the needle lumen. For a 1 ml syringe this has been measured to be at least approximately 0.08 ml and the waste is worsened if the needle is exchanged during the series of injections.

Also, conventional neurotoxin syringes are not graduated in unit dosing which is how users are trained to inject neurotoxin. Further, if conventional neurotoxin syringes do not have Luer lock connections, the needle can come dislodged from the syringe during an injection and can cause an injury to the patient and waste the costly neurotoxin.

Therefore, many practitioners have circumvented these problems by using insulin syringes that are either 30 unit or 50 unit syringes that can accommodate the 10 unit/0.1 ml concentration to get a true 1:1 injection ratio. Insulin syringes can only be used for unit dosing at the 1 ml dilution of neurotoxin because the resulting concentration is the same as subcutaneous insulin at 1 unit/0.01 ml. In all other concentrations of neurotoxin that are injected with insulin syringes, each gradation no longer represents 1 unit of neurotoxin.

Most of the insulin syringes are low-waste and have permanent, non-removable needles. Insulin syringes are designed for single-injection only in the subcutaneous tissue plane and are not engineered for the multiple percutaneous punctures required of neurotoxin injections. Insulin needles are not sufficiently engineered to withstand multiple percutaneous punctures. Insulin syringes are small and it is very difficult to read the gradations and they are awkward for larger hands. The needles dull quickly and cannot be changed for a sharper needle. The length of the needle is designed for subcutaneous injection and not intramuscular injection (indicated for neurotoxin) and it is too short for many patients thus producing a poor result. Multiple syringes would be necessary if greater than 30 or 50 units were to be injected losing time exchanging syringes and the cost of additional syringes.

Another problem with insulin syringes with permanent needles is that if the neurotoxin is aspirated from the vial through the elastomeric top, the needle will be dulled even further for multiple injections. Many practitioners remove the metal seal and elastomeric stopper of the vial and insert the entire clean, but not sterile, syringe into the vial to aspirate the desired amount of neurotoxin and then replace the elastomeric stopper. This procedure contaminates the vial each time it is done (which is typically three times or more per vial). This is not standard protocol for a sterile, multi-use vial and greatly increases the risk of injection site infection and bacterial contamination of the neurotoxin left in the vial. Another problem with insulin syringes with permanent needles is that if the needle gets dull and painful during the series of injections there is no way to exchange the needle for a sharper one or easily transfer the neurotoxin to another syringe so the costly neurotoxin is not wasted. Unfortunately, the injections often continue at the expense and discomfort of the patient until the syringe is empty.

Non-low-waste syringes in this volume range include 1 ml syringes and some insulin syringes. The measured waste in the conventional non-low-waste syringe includes approximately 0.04 ml in the tip and approximately 0.04 ml in the needle hub. Thus, at the end of a series of injections approximately 0.08 ml of fluid is left in the syringe tip and needle hub. This translates into a significant loss of neurotoxin and cost to the practitioner depending upon the amount of diluent used and the resultant concentration of the neurotoxin injected. In some estimates, the lost or wasted neurotoxin can be in the tens of thousands of dollar per user per year. Further, although 1 ml low-waste syringes are available, they are not gradated for unit injection, which is how most users are trained to inject. Additionally, conventional low-waste 1 ml syringes only prevent neurotoxin waste in the syringe tip, not the needle hub, and thus, costly neurotoxin is still wasted.

In view of the preceding, there is a need in the art for a low-waste neurotoxin syringe and needle that can indicate unit dosage at a plurality of neurotoxin concentration levels.

SUMMARY

Described herein is a needle and syringe assembly for injecting a fluid into a patient and more particularly to a low-waste syringe with at least one interchangeable needle.

In one aspect, the syringe can comprise a hollow body having an inner diameter and an end wall closing a forward end of the body. In another aspect, a rear end of the body can be open and a piston means in reciprocal sealing engagement with an inner wall of the body can define a fluid chamber in the body. The fluid chamber can be configured for selectively containing a medication, such as for example and without limitation, a neurotoxin, within the fluid chamber.

At least a portion of the syringe can be formed from a clear polymeric material, according to one aspect. In another aspect, an outer wall of the body can be marked and/or labeled to indicate the type of fluid contained in the chamber. For example, if the fluid is a neurotoxin, the outer wall of the body can be marked and/or labeled to indicate the type of neurotoxin and/or the amount of diluent used in reconstituting the neurotoxin. In one aspect, hatch marks can be marked and/or labeled on the outer wall of the body to indicate the amount of fluid and/or the concentration of the fluid contained in the chamber. For example, the hatch marks can be color coded such that different colored hatch mark can indicate dosage amounts based on different concentrations. The clear body allows the user to compare the fluid level in the chamber to the hatch mark on the body.

In one aspect, a syringe tip can be mounted and/or formed on the end wall of the syringe to define an interior void. An aperture in the end wall of the body can place the interior void of the syringe tip in sealed fluid communication with the fluid chamber of the body. In another aspect, the syringe tip can be configured to matingly engage and secure a needle assembly to the syringe. In a further aspect, the syringe tip can form at least a portion of an inverted cone. In this aspect, at least a portion of the syringe tip can be substantially frusto-conical in shape defining a frusto-conical interior void.

The piston means can comprise a plunger and a piston cap. In one aspect, the plunger can be formed from a substantially cylindrical shaft and the piston cap can be securely attached to an end of the shaft. In another aspect, the piston cap can be formed from an elastomer wherein at least a portion of the piston cap has an outer diameter substantially equal to the inner diameter of the body of the syringe. However, in a further aspect, at least a portion of the piston cap can have an outer diameter slightly greater than the inner diameter of the body of the syringe. In yet another aspect, a distal end of the piston cap can be configured to complementary engage the end wall of the body of the syringe. That is, the distal end of the piston cap can be sized and shaped so that when in use, the distal end of the piston cap contacts the end wall. In this aspect, when in use and the piston cap contacts the end wall of the body, there are substantially no gaps or "dead spaces" formed between the end wall and the distal end of the piston cap. This allows substantially allow of the fluid contained in the fluid chamber to be ejected from the chamber through the syringe tip.

In one aspect, the at least one needle assembly can comprise an elongate needle and a polymeric needle hub configured to support the needle and couple the needle to the syringe so that an interior lumen of the needle is in fluid communication with the fluid chamber of the syringe. In another aspect, the needle can be a conventional needle, such as a 25G needle, a 32G needle and the like. The needle hub can comprise a substantially cylindrical hollow needle base having internal threads configured to matingly engage with flanges on the syringe as in a conventional Luer-lock engagement. In one aspect, a frusto-conical member can be formed and/or positioned in the substantially cylindrical hollow needle base of the needle hub. In this aspect, the frusto-conical member can be configured to matingly engage the frusto-conical void defined in the syringe tip. When the threads of the needle hub engage the syringe, the frusto-conical member of the needle hub can create a fluid-tight seal with the frusto-conical void of the tip of the syringe, so that when in use, there are substantially no gaps or "dead spaces" formed between the needle hub and the syringe.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

These and other features of the preferred embodiments of the invention will become more apparent in the detailed description in which reference is made to the appended drawings wherein.

DETAILED DESCRIPTION

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof. As used throughout, the singular forms "a," "an" and "the" include plural referents unless the context clearly dictates otherwise. Thus, for example, reference to "a needle" can include two or more such needles unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

As used herein, the term "fluid" can refer to any medication such as a neurotoxin, insulin, tuberculin and the like. Additionally, the term "fluid" can refer to a solution containing a diluent and any medication such as a neurotoxin, insulin, tuberculin and the like.

Figure 1A:
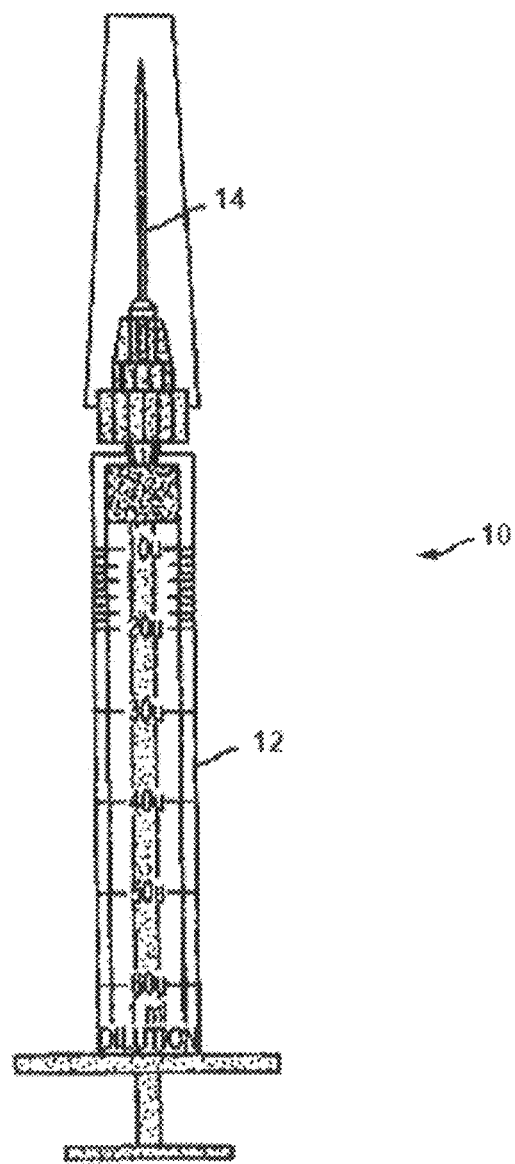
FIGS. 1A and 1B are elevational views of embodiments of a needle assembly and syringe for injecting a fluid contained in the syringe into a patient.
Figure 1B:
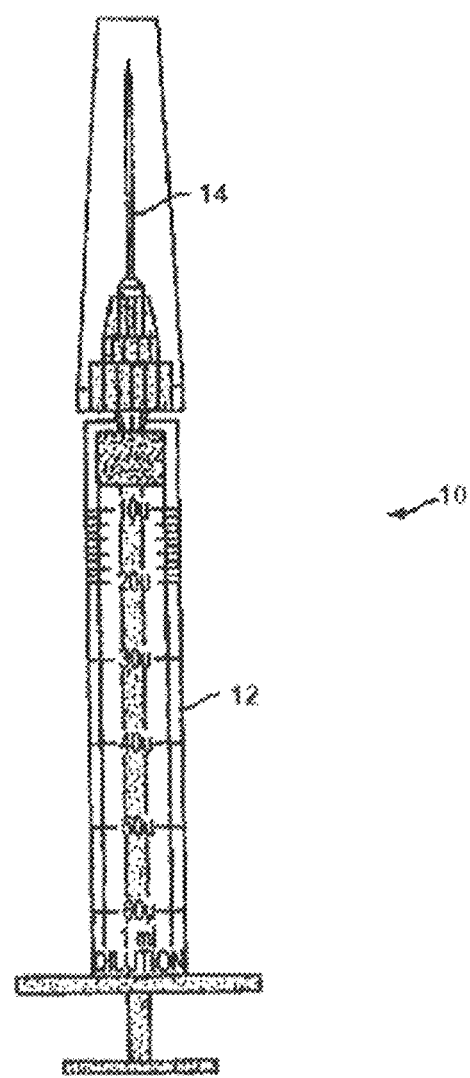

A needle and syringe assemblage 10 for injecting a fluid into a patient is provided, according to various aspects and as illustrated in FIGS. 1A and 1B. In one aspect, the needle and syringe assemblage comprises a syringe 12 and at least one needle assembly 14. In another aspect, the needle and syringe assemblage 10 comprises a low-waste syringe and at least one interchangeable needle. In a further aspect, the syringe 12 can be a low-waste, single-use syringe with at least one interchangeable needle assembly 14.

Figure 2:
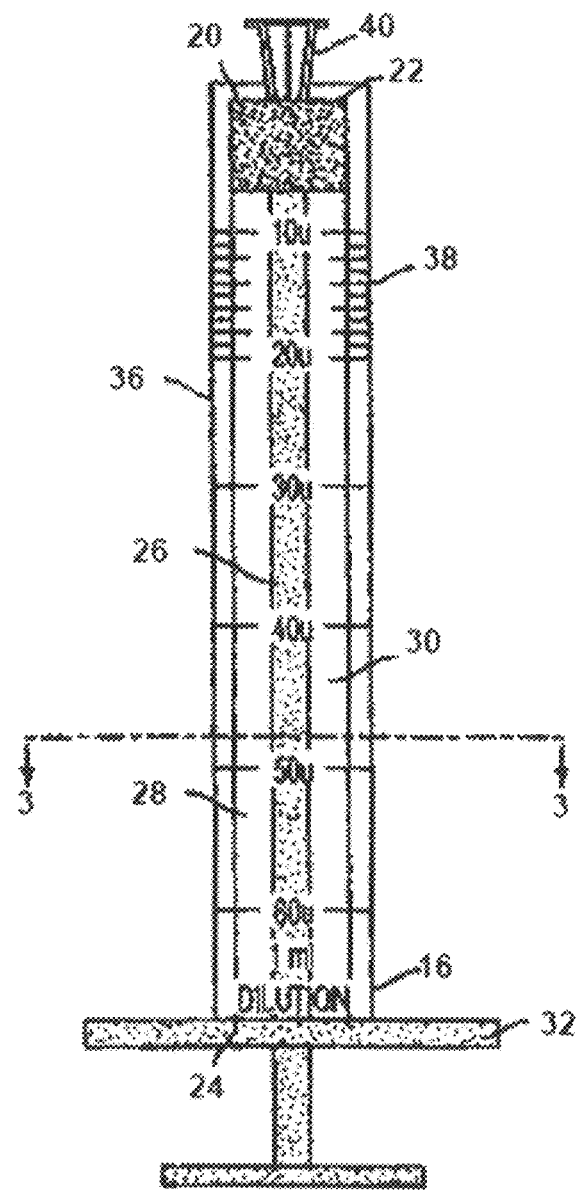
FIG. 2 is an elevational view of the syringe of FIG. 1, according to one aspect.
Figure 3:
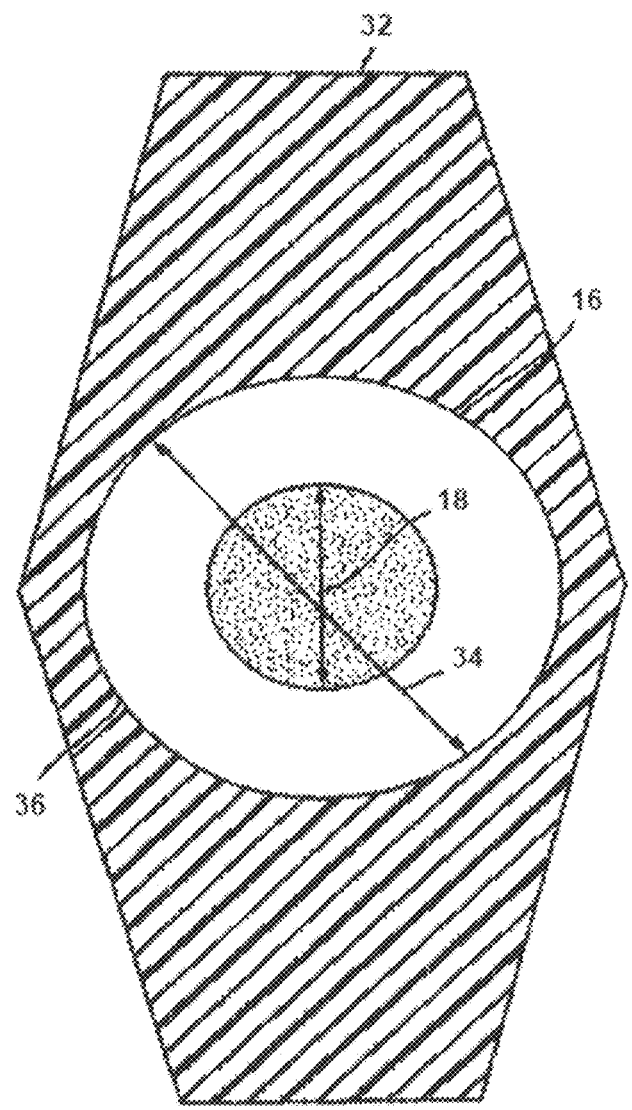
FIG. 3 is a cross-sectional view of the syringe of FIG. 2, taken along line 3-3.
Figure 4:
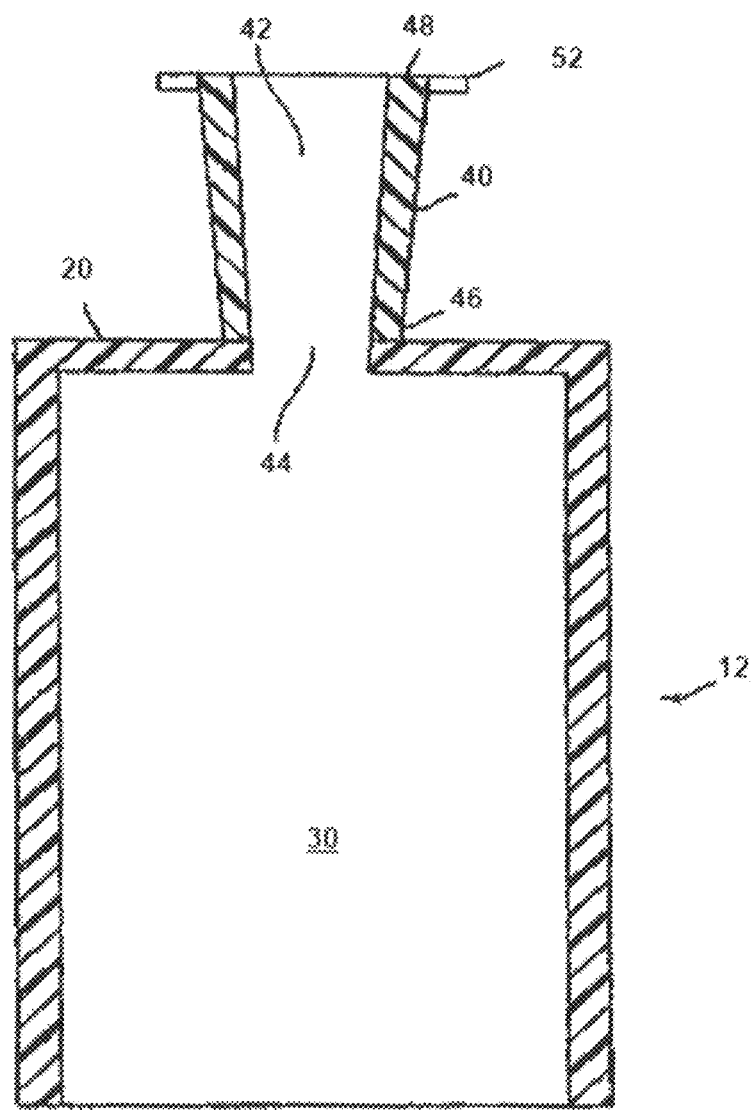
FIG. 4 is an elevational view of a portion of the syringe of FIG. 2, according to one aspect.
Figure 5:
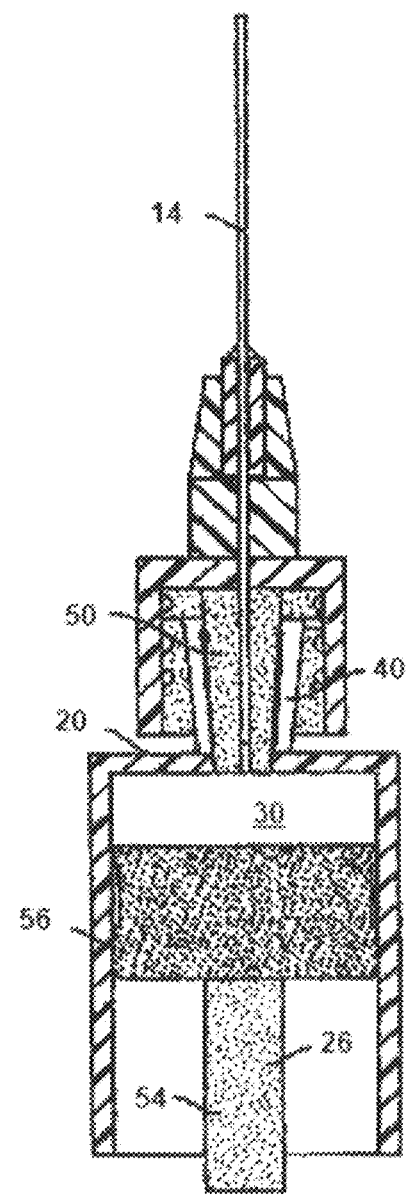
FIG. 5 is an elevational view of the needle assembly of FIG. 1 coupled to the syringe, according to one aspect.

Referring now to FIGS. 2 and 3, in one aspect, the syringe 12 can comprise a hollow body 16 having an inner diameter 18 and an end wall 20 that can close the body at a forward end 22 of the body. In another aspect, a rear end 24 of the body 16 can be open and a piston means 26 in reciprocal sealing engagement with an inner wall 28 of the body can define a chamber 30 in the body. The chamber can be configured for selectively containing a fluid, such as for example and without limitation, medication, within the chamber 30. The syringe 12 can further comprise at least one finger flange 32 formed or positioned adjacent the open rear end of the body 16, according to another aspect.

In one aspect, the body 16 of the syringe 12 can have a length of less than about 7 cm, about 7.0 cm, about 7.15 cm, about 7.25 cm, about 7.4 cm, about 7.5 cm, about 7.65 cm, about 7.75 cm, about 7.85 cm, about 8.0 cm, about 8.15 cm, about 8.25 cm, about 8.4 cm, about 8.5 cm, about 8.65 cm, about 8.75 cm, about 8.85 cm, about 9.0 cm, about 9.15 cm, about 9.25 cm, about 9.4 cm, about 9.5 cm, about 9.65 cm, about 9.75 cm, about 9.85 cm, about 10.0 cm, or greater than about 10.0 cm.

In another aspect, an outer diameter 34 of the body 16 can be less than about 0.25 cm, about 0.25 cm, about 0.3 cm, about 0.35 cm, about 0.4 cm, about 0.45 cm, about 0.5 cm, about 0.55 cm, about 0.6 cm, about 0.65 cm, about 0.7 cm, about 0.75 cm, about 0.8 cm, about 0.85 cm, about 0.9 cm, about 0.95 cm, about 1.0 cm, about 1.05 cm, about 1.1 cm, about 1.15 cm, about 1.2 cm, about 1.25 cm, about 1.3 cm, about 1.35 cm, about 1.4 cm, about 1.45 cm, about 1.5 cm, about 1.55 cm, about 1.6 cm, about 1.65 cm, about 1.7 cm, about 1.75 cm, about 1.8 cm, about 1.85 cm, about 1.9 cm, about 1.95 cm, about 2.0 cm or greater than about 2 cm. In this aspect, it is contemplated that the outer diameter of the body 16 can be a substantially constant diameter, and the inner diameter 18 of the body can be varied to change the volume capacity of the chamber 30 of the body 16. For example, the inner diameter can be a predetermined diameter so that the volume capacity of the body is a predetermined level. Thus, two syringes having the same body size can contain a different amount of fluid based on the volume capacity of the chamber.

In one aspect, at least a portion of the syringe 12 can be formed from a clear polymeric material. In another aspect, the body 16 of the syringe can be molded from a hard, clear plastic. An exterior surface or outer wall 36 of the body can be printed, marked and/or labeled to indicate the type of fluid contained in the chamber. For example, if the fluid is a neurotoxin, the outer wall of the body 16 can be marked and/or labeled to indicate the type of neurotoxin and/or the amount of diluent used in reconstituting the neurotoxin. In a further aspect, hatch marks 38 can be printed, marked and/or labeled on the outer wall 36 of the body to indicate the amount of fluid contained in the chamber 30. In yet another aspect, the hatch marks can be positioned or printed on either side of a centerline of the body 16 so that both left handed and right handed users of the syringe can easily see the hatch marks 38. In this aspect, the hatch marks can be color coded such that different colored hatch mark 38 can indicate different fluid concentrations.

In one aspect, the hatch marks 38 on the exterior surface or outer wall 36 of the syringe 12 can indicate a concentration marking scale. That is, hatch marks can be printed or marked on the syringe to refer to a concentration of fluid contained in the chamber 30 of the syringe. For example, each hatch mark can refer to a volume of medication per volume of diluent. In another aspect, the hatch marks 38 on the outer wall of the syringe can be indicative of the relative units of medication per volume of diluent. In an example and with reference to FIG. 2, the "10 u", "20 u" . . . markings can indicate the units of neurotoxin per volume of diluent. This allows the user of the syringe to easily "unit dose" the patient as users have conventionally been trained. As can be appreciated, different syringes can be provided to a user based on the user's desired medication concentration level.

For example, if 100 units of neurotoxin were diluted with 1 ml of diluent, the solution would have a concentration of 10 units per 0.1 ml or 1 unit per 0.01 ml. The syringe 12 could have a chamber 30 sized to hold 60 units and a total volume of 0.6 ml. The hatch marks 38 on the body 16 of the syringe 12 could be unit marked at 1 or 2 unit increments and each unit increment could correspond to 0.01 ml of the solution. In another example, if 100 units of neurotoxin were diluted with 2 ml of diluent, this would create a solution having a concentration of 5 units per 0.1 ml or 1 unit per 0.02 ml. In this example, the syringe could have a chamber sized to hold 60 units and a total volume of 1.2 ml. That is, the inner diameter 18 of the body could be sized so that the chamber 30 could contain 1.2 ml of medication. In this aspect, the hatch marks on the body 16 of the syringe 12 could be unit marked at 1 or 2 unit increments and each unit increment could correspond to 0.02 ml of the solution. In another example, if 100 units of neurotoxin were diluted with 2.5 ml of diluent (such as, for example, on label for Botox®) this would create a concentration of 4 units per 0.1 ml or 1 unit per 0.025 ml. In this example, the chamber 30 of the body could hold 50 units and a total volume of 1.25 ml. The hatch marks 38 on the syringe 12 could be unit marked at 1 or 2 unit increments and each unit increment could correspond to 0.025 ml. In still another example, if 100 units of neurotoxin were diluted with 4 ml of diluent, this solution created would have a concentration of 2.5 units per 0.1 ml or 1 unit per 0.04 ml. The chamber 30 of the syringe could be sized to hold 30 units and a total volume of 1.2 ml. The hatch marks on the syringe 12 could be unit marked at 1 or 2 unit increments and each unit increment would correspond to 0.04 ml. It is of course contemplated that syringes could be sized and marked according to any predetermined volume and/or dilution amount.

With reference to FIGS. 2, 4, 5 and 6 in one aspect, a syringe tip 40 can be mounted and/or formed on the end wall 20 of the syringe 12 so that the syringe tip extends longitudinally away from the body 16 of the syringe. In this aspect, an interior void 42 can be defined in the syringe tip, and an aperture 44 in the end wall can place the interior void of the syringe tip in sealed fluid communication with the chamber 30 of the body 16. The syringe tip 40 can be configured to matingly engage and secure a needle assembly 14 to the syringe.

The syringe tip 40 can be at least a portion of an inverted cone, according to one aspect. That is, at least a portion of the syringe tip can be substantially frusto-conical in shape. In another aspect, a first end 46 of the syringe tip having a first diameter can be coupled to the end wall 20 of the body 16, and a second end 48 of the syringe tip 40 can be positioned a predetermined distance from the end wall and having a second diameter that is greater than the first diameter. In yet another aspect, the interior void 42 defined in the syringe tip can define a substantially frusto-conical void that is configured to receive a frusto-conical member 50 of a needle assembly 14 (described more fully below). In a further aspect, two flanges 52 can project radially away from the second end 48 of the syringe tip. The flanges can be configured to selectively engage the Luer-lock mechanism of a needle assembly, as known in the art.

Figure 16:
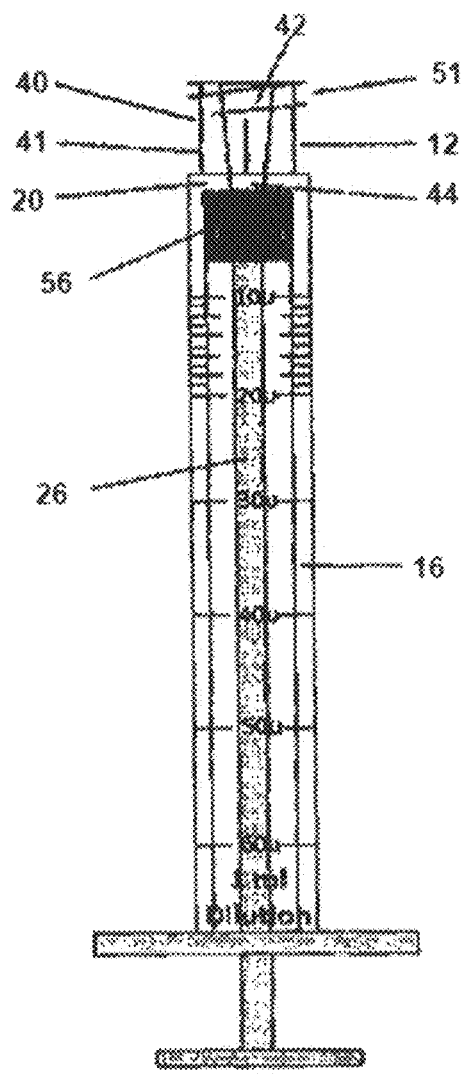
FIG. 16 is a side elevational transparent view of a syringe, showing a syringe tip configuration in which the external surface of the syringe tip is substantially cylindrical in shape with a conventional thread formed thereon for conventional coupling to a needle assembly, according to one aspect.

As shown optionally in FIG. 16, the syringe tip 40 can have a substantially cylindrical outer surface shape. In this aspect, it is contemplated that the outer surface of the syringe tip can have a conventional helical threaded surface defined thereon that can cooperatively receive a complementarily threaded base 86 of the needle hub 80, as known in the art. In yet another aspect, the interior void 42 defined in the syringe tip can define a substantially frusta-conical void that is con-figured to receive a frusto-conical member 50 of a needle assembly 14 (described more fully below).

Figure 17:
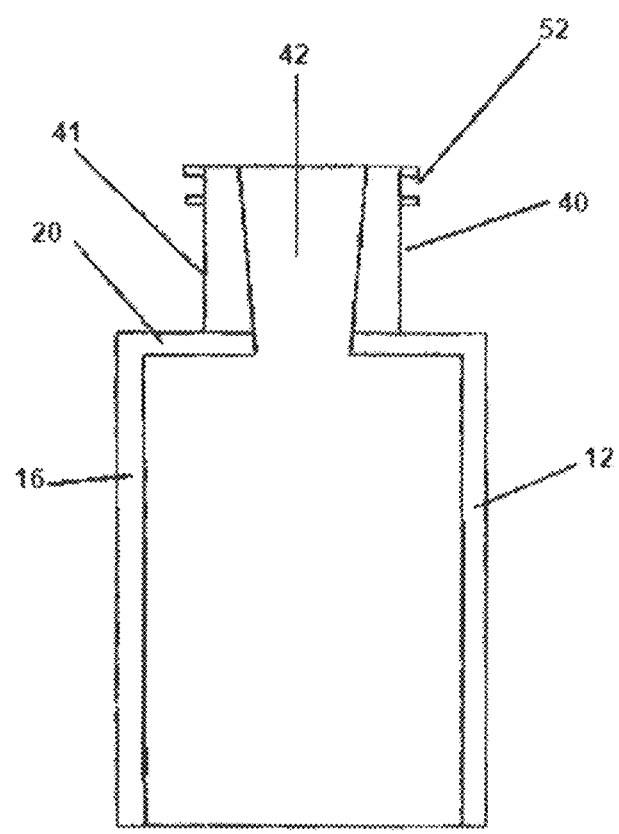
FIG. 17 is a cross-sectional view of a syringe, showing a syringe tip configuration in which the external surface of the syringe tip is substantially cylindrical in shape with a conventional thread formed thereon for conventional coupling to a needle assembly, according to one aspect.
Figure 18:
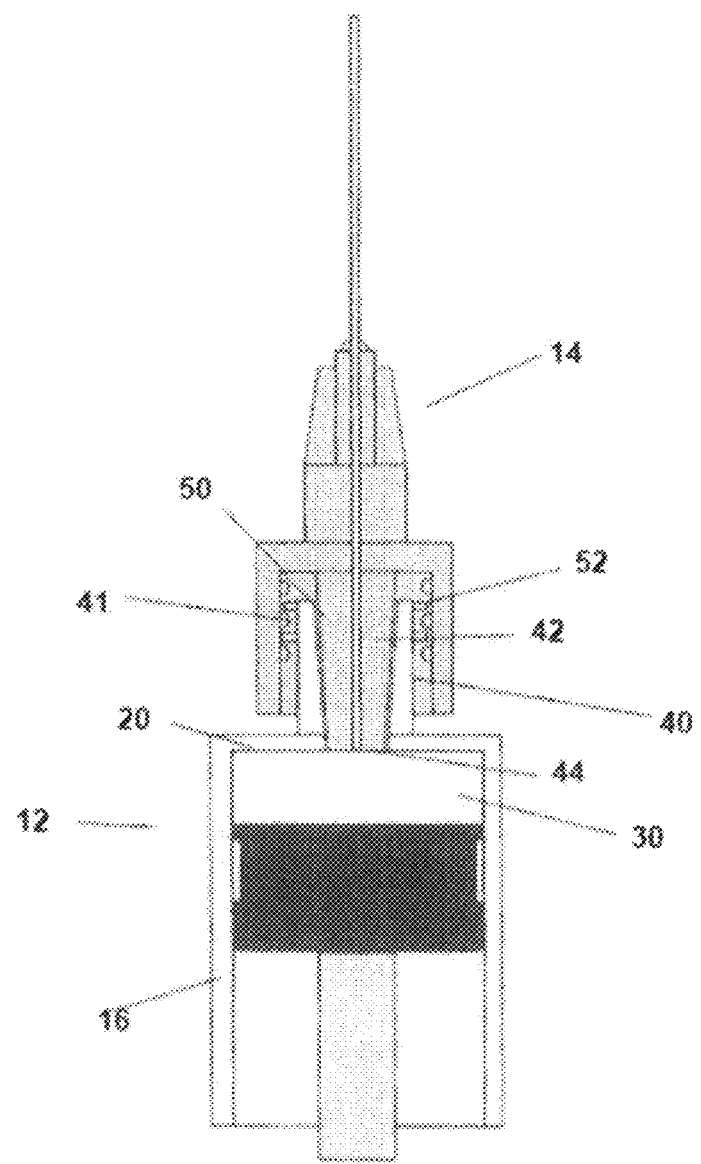
FIG. 18 is a cross-sectional view of the syringe of FIG. 17, showing a needle assembly conventionally coupled to the conventional thread formed thereon the external surface of the syringe tip and a plunger disposed therein the syringe, according to one aspect.
Figure 19:
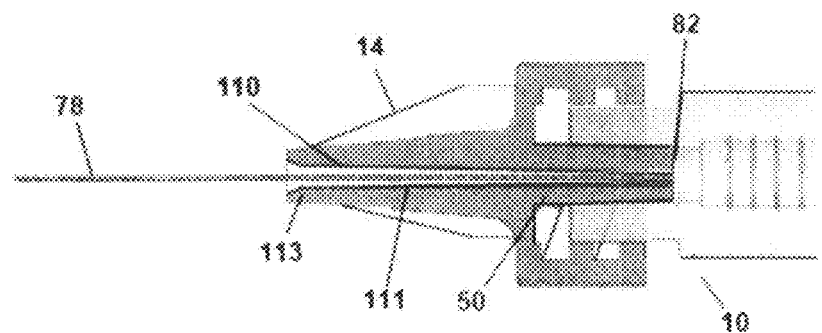
FIG. 19 is a cross-section view of a needle assembly conventionally coupled to the conventional thread formed thereon the external surface of the syringe tip and a plunger disposed therein the syringe, according to one aspect and showing a central bore of a frusto-conical member of a needle hub 80 having a frusto-conical shape that expands outwardly, relative to a longitudinal axis of the needle hub, from proximate a proximal end of the needle hub to a distal end of the needle hub. AS shown, the central bore can define at least two progressively increasing tapering frusto-conical shapes, relative to the longitudinal axis of the needle hub, which is typically aligned with the mounted needle.
Figure 20:
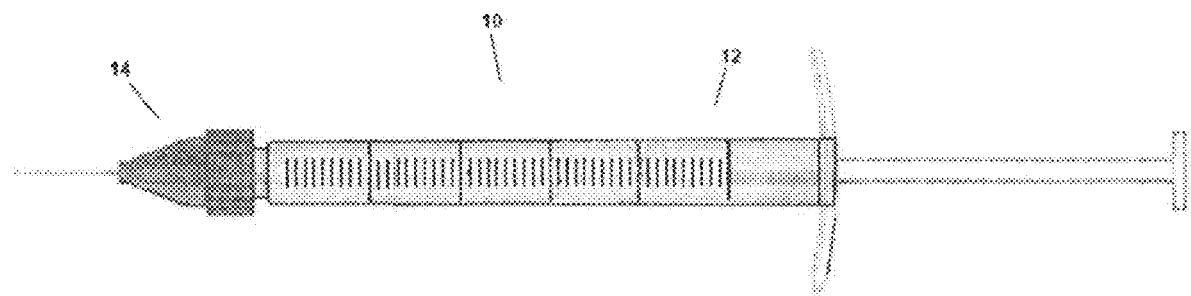
FIG. 20 is an elevational view of one aspect of a needle assembly conventionally coupled to the conventional thread formed thereon the external surface of the syringe tip and a plunger disposed therein the syringe of FIG. 19, according to one aspect.
Figure 21:
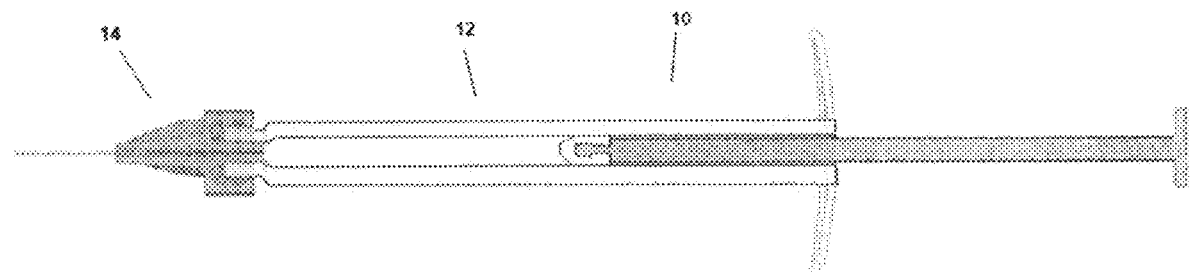
FIG. 21 is a cross-sectional view of the needle assembly needle assembly conventionally coupled to the conventional thread formed thereon the external surface of the syringe tip and a plunger disposed therein of FIG. 20, according to one aspect.
Figure 22:
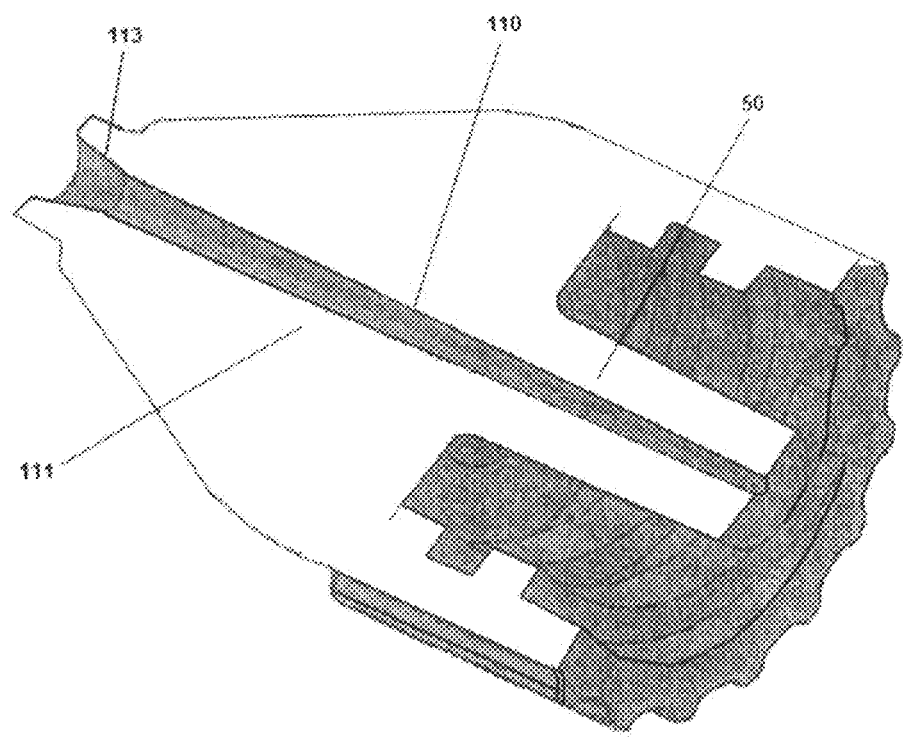
FIG. 22 is a perspective cross-sectional view of the needle assembly of FIG. 19.

In a further aspect shown in FIGS. 16-18, the syringe can have a syringe tip 40 that has a substantially cylindrical outer surface shape 41. Conventionally threading 51 can be formed on the outer surface of the syringe tip that is adapted to be conventionally coupled to needle assemblies, IV lines, and other conventional fluid medical couplers, according to optional aspects. In this particular aspect, it is contemplated that the interior void 42 defined in the syringe tip can define a substantially frusto-conical void that is configured to receive a frusto-conical member 50 of a needle assembly 14 (described more fully below). In a further exemplary aspect, and as shown in FIGS. 17 and 18, two flanges 52 can project radially away from the second end 48 of the syringe tip. The flanges can be configured to selectively engage the Luer-lock mechanism of a needle assembly, as known in the art.

Figure 6:
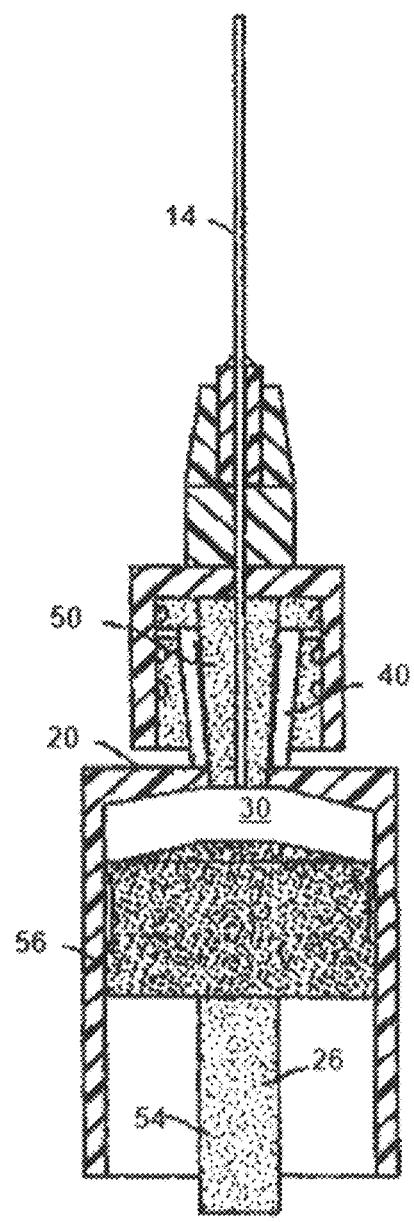
FIG. 6 is an elevational view of the needle assembly coupled to the syringe, according to an alternative aspect.
Figure 7:
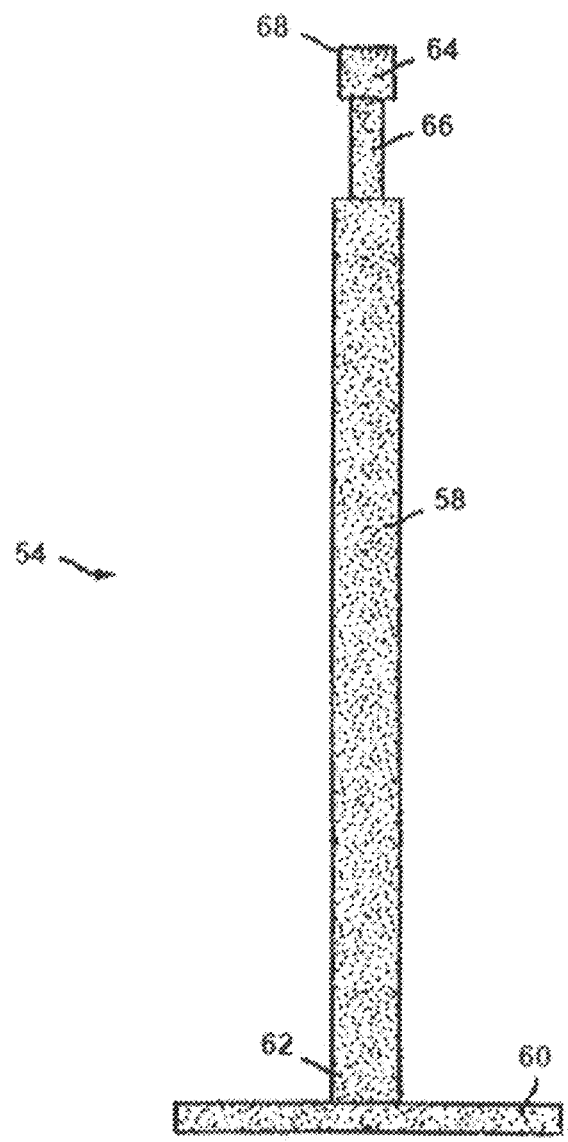
FIG. 7 is an elevational view of a plunger of the syringe of FIG. 1, according to one aspect.
Figure 8:
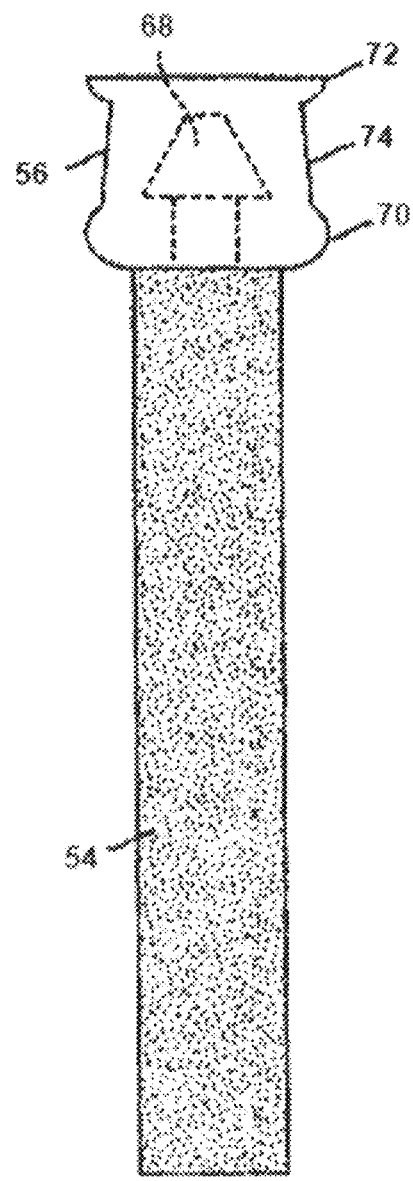
FIG. 8 is an elevational view of a plunger of the syringe of FIG. 1, in which the broken lines indicate a head of the plunger, according to one aspect.

As illustrated in FIGS. 5-8, the piston means 26 can comprise a plunger 54 and a piston cap 56. In one aspect, the plunger can be formed from a substantially cylindrical molded shaft 58. The shaft can have an outer diameter smaller than the inner diameter 18 of the body 16 of the syringe 12 so that the plunger 54 can move within the chamber 30 of the body. A thumb surface 60 can be formed on a proximal end 62 of the shaft configured to provide a flat surface for the user of the syringe to press and move the plunger 54 (and the piston cap 56) within the chamber. In another aspect, a portion of a distal end 64 of the plunger can have an outer diameter less than the outer diameter of the shaft, forming a plunger neck 66. In this aspect, the neck can be configured for attachment of the piston cap 56 to the shaft. A plunger head 68 can be positioned adjacent to the neck. In one aspect, the plunger head can be substantially cylindrical having an outer diameter substantially the same as the plunger shaft 58, as illustrated in FIG. 7. Alternatively, in another aspect, the plunger head 68 can be substantially frusto-conical (as illustrated in FIG. 8), in which a portion of the head has an outer diameter substantially the same as the plunger shaft 58.

The piston cap 56 can be formed from a molded elastomer having a proximal end 70 and a distal end 72. In one aspect, the piston cap can have an outer diameter substantially equal to the inner diameter of the body 16 of the syringe 12. In a further aspect, at least a portion of the piston cap 56 can have an outer diameter slightly greater than the inner diameter 18 of the body of the syringe. In still another aspect, the proximal end 70 of the piston cap can have an outer diameter slightly greater than the outer diameter of the distal end 72 of the piston cap 56. In yet another aspect, a central portion 74 of the piston cap can have an outer diameter less than either or both the outer diameter of the distal end and the proximal end of the piston cap 56.

According to one aspect, the distal end 72 of the piston cap 56 can be configured to complementary engage the end wall 20 of the body 16 of the syringe 12. That is, the distal end of the piston cap can be sized and shaped so that when in use, the distal end 72 of the piston cap 56 contacts the end wall 20, and that that when contacting each other, there are substantially no gaps or "dead spaces" formed between the end wall and the distal end of the piston cap. For example, if the end wall 20 of the body 16 is substantially planar or flat, the distal end 72 of the piston cap 56 can be substantially planar or flat so that substantially all the fluid contained in the chamber 30 is ejected from the chamber through the needle 78, as described more fully below.

In one aspect, an inner bore can be defined in the piston cap 56 configured to matingly engage the plunger head 68 and/or the plunger neck 66 of the plunger shaft 58. That is, due to the elastic nature of the piston cap 56, the inner bore of the piston cap can be positioned on and "snap" to the head and/or neck of the piston shaft. For example and with reference to FIG. 7, the piston cap 56 can snap onto the plunger shaft 58 and can be secured in position by its elastic properties.

In a further optional aspect, and as shown in FIG. 6, portions of the walls defining the distal end of the chamber 30 of the body 16 of the syringe can be tapered distally and inwardly toward the aperture 44 in the end wall. In this aspect, it is contemplated that the distal end of the piston cap of the plunger will be complementarily shaped such that, when the plunder is fully depressed distally toward the end wall, the distal end of the piston cap of the plunger is in flush contact with the formed end wall of the chamber to reduce or eliminate any dead space within the chamber of the body in this depressed position.

In use, described more fully below, the outer diameter of at least a portion of the piston cap 56 can tightly engage the inner diameter 18 of the body 16 of the syringe 12, forming a fluid-tight seal. Furthermore, the outer diameter of the proximal end 70 and/or the distal end 72 of the piston cap 56 can provide stability to the plunger 54 by preventing or restricting rotational movement between the plunger and the body. In another aspect, the seal formed between the piston cap and the inner diameter of the body 16 can provide desirable injection resistance to help control the injection of small amounts of fluid from the syringe 12.

Figure 9:
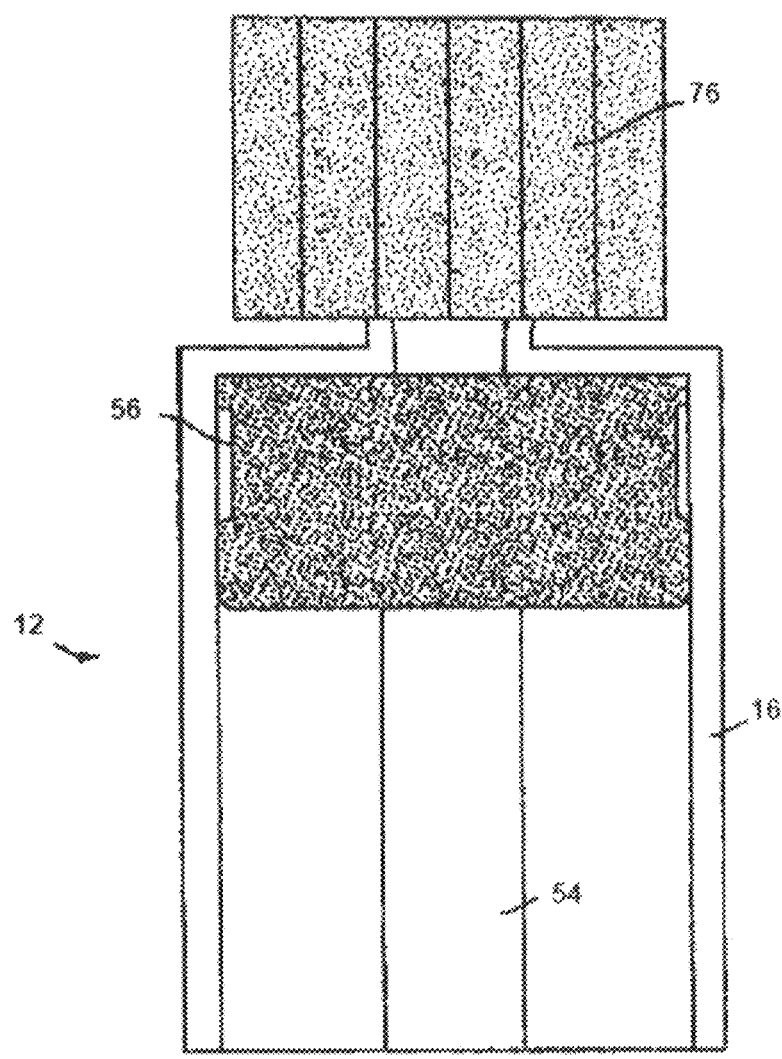
FIG. 9 is an elevational view of a protective cover of the syringe of FIG. 1, according to one aspect.

Optionally, and as shown in FIG. 9, the syringe 12 can further comprise a protective cover 76. In one aspect, the protective cover can have inner threads similar to conventional Luer lock threads to selectively couple the protective cover to the forward end 22 and/or the syringe tip 40 of the syringe. When coupled to the syringe 12, the protective cover 76 can protect the syringe tip 40 and maintain the sterility of the chamber 30 of the syringe itself. It is contemplated that the protective cover can be color coded for safety depending upon, for example and without limitation, the amount of diluent used and the resulting concentration of fluid to be injected.

With reference to FIGS. 10-12 and 18-22, the at least one needle assembly 14 can comprise at least one of the needle 78 itself and a polymeric needle hub 80 configured to support the needle and attach the needle to the syringe.

Figure 11:
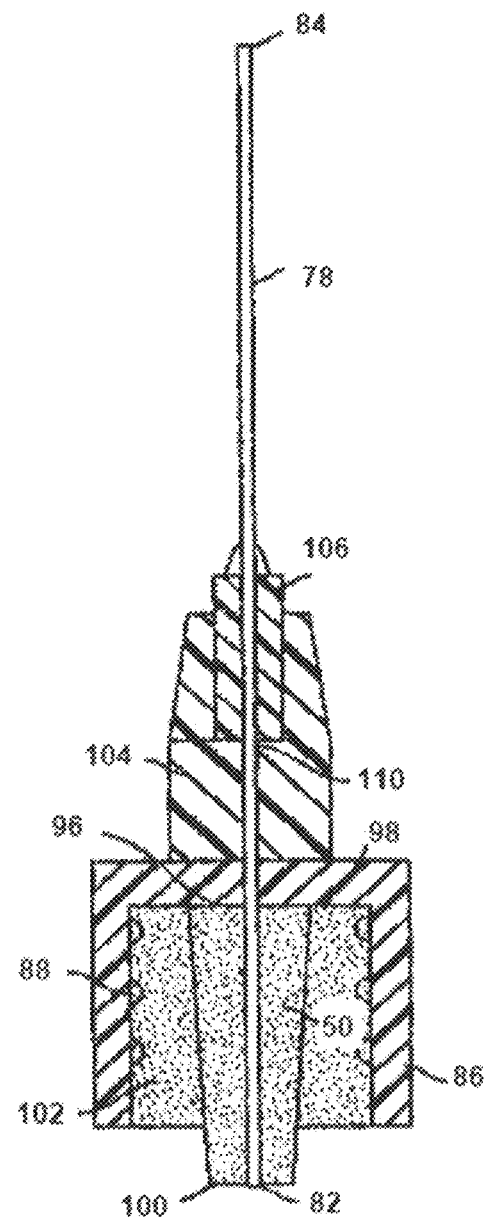
FIG. 11 is a cross-sectional view of the needle assembly of FIG. 10, according to one aspect.
Figure 12:
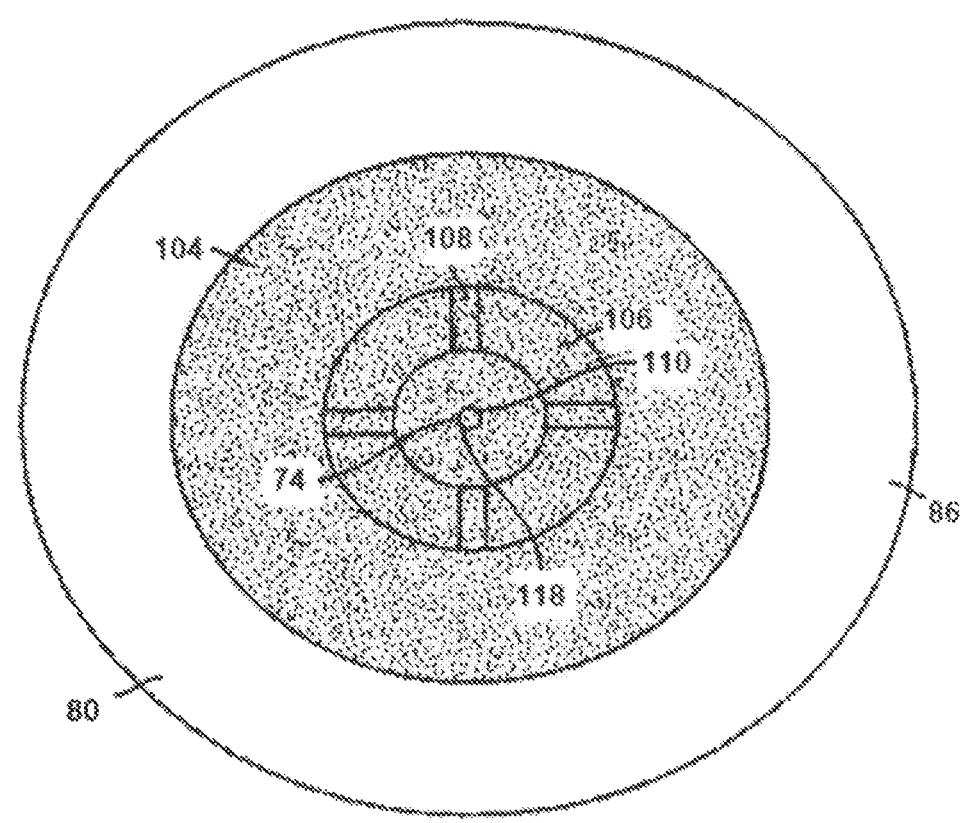
FIG. 12 is a top plan view of needle assembly of FIG. 10, according to one aspect.

In one aspect, the needle 78 can be at least one of an approximately 25G ½" length needle and a 32G ½" length needle. For example, a needle 78 for aspiration can be the 25G needle to allow for minimal waste of medication while still having sufficient flow characteristics so as to not impede filling of the syringe 12. In another example, a needle designed for injection can be a 32G needle 78 having excellent flow characteristics and long enough for intramuscular injections. As known to one of skill in the art, a 32G needle does not easily bend and can remain sharp after multiple percutaneous punctures. The 32G needle can be injected relatively pain free and can leave negligible medication waste in the syringe. In one aspect, and as shown in FIG. 11, a proximal end 82 of the needle can be blunt and a distal end 84 of the needle can be beveled or blunt. It is contemplated that the needle can be color coded to correspond to existing needle gauge convention.

In one aspect, the needle 78 can be an elongate needle that passes through the needle hub 80. In another aspect, the needle hub can comprise a substantially cylindrical hollow needle base 86 having internal threads 88. In this aspect, the internal threads can be configured to matingly engage with the flanges 52 of the syringe as in a conventional Luer-lock engagement. For example, the internal threads 88 of the base 86 of the needle hub 80 can be configured so that approximately a 180 degree turn of the needle hub relative to the body 16 of the syringe can fully engage and secure the needle 78 into position on the syringe 12. As can be appreciated, the Luer-lock mechanism can keep the needle-syringe assemblage 10 stable so that the needle 78 will not dislodge during injection causing possible injury and loss of expensive medication. Furthermore, the Luer-lock mechanism of the needle hub 80 and the flange of the syringe can allow for rapid, multiple needle changes as desired. It is of course contemplated that the exterior surface of the needle hub can be conventionally configured to allow for conventional connection to desired medical devices, for example and not meant to be limiting, to Luer-lock fittings and the like.

Figure 10:
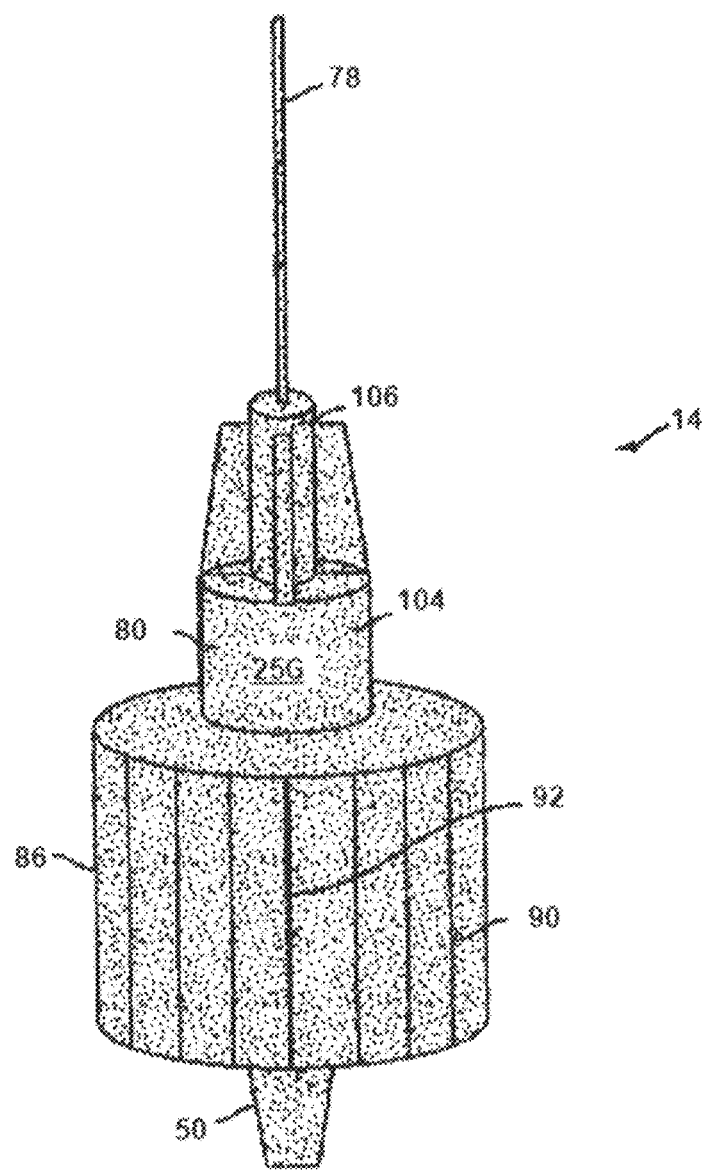
FIG. 10 is a perspective view of the needle assembly of FIG. 1, according to one aspect.

As shown in FIG. 10, in one aspect, the base 86 of the needle hub 80 can comprise at least one outer longitudinal groove 90 configured to aid in handling and securely fastening the needle hub to the syringe tip 40. In another aspect, the base can further comprise an alignment mark 92 so that when the needle base is securely attached to the syringe 12, the distal end 84 of the needle 78 can be rotated to a desired position (i.e., if the distal end is beveled, the bevel is in a desired orientation relative to the syringe) and in line with the syringe markings when holding the syringe 12 for injection. That is, in this aspect, the alignment mark 92 on the needle base can be in line with the needle bevel and in "front" of the syringe after the needle hub 80 is fully engaged and rotated into position on the syringe tip.

In one aspect, the frusto-conical member 50 of the needle assembly 14 can be formed and/or positioned in the substantially cylindrical hollow needle base 86 of the needle hub 80. In another aspect, the frusto-conical member can comprise a distal end 96 having a first diameter coupled to an end wall 98 of the base and a proximal end 100 having a second diameter extending into the hollow cylinder 102 of the base a predetermined distance. In this aspect, the second diameter can be less than the first diameter. In a further aspect, the proximal end 100 of the frusto-conical member 50 of the needle hub can extend beyond the hollow cylinder of the base (as illustrated in FIGS. 10 and 11).

In one aspect, the frusto-conical member 50 of the needle hub 80 can be sized and shaped to matingly engage the substantially frusto-conical void 42 of the syringe tip 40. That is, the frusto-conical member of the needle hub can be configured to slide into the frusto-conical void of the tip of the syringe 12. When the Luer-lock mechanism of the needle hub 80 engages the syringe, the frusto-conical member 50 of the needle hub can create a fluid-tight seal with the frusto-conical void 42 of the tip 40 of the syringe.

In one aspect, the needle hub 80 can further comprise at least two progressively smaller cylinders 104, 106 coupled to the needle base 86. In one aspect, these progressively diminishing cylinders can allow for better visualization of the puncture site and can provide axial stability for the needle 78 itself. In another aspect, a plurality of flanges 108 can be spaced from each other and positioned adjacent the smallest cylinder. In this aspect, the flanges can also provide axial stability for the needle.

In one aspect, a central bore 110 can be defined in and extend through the cylinders 104, 106, the end wall 98 of the needle base 86, and the frusto-conical member 50 of the needle base. The central bore can be sized to allow a needle 78 to be positioned therein. In another aspect, the needle can be positioned in the central bore such that a proximal end 82 of the needle can be substantially aligned with the proximal end 100 of the frusto-conical member of the needle base. Optionally, however, the proximal end of the needle 78 can extend beyond the proximal end 100 of the frusto-conical member 50, or the proximal end of the frusto-conical member can extend beyond the proximal end 82 of the needle. In a further aspect, the distal end 84 of the elongate needle can protrude from the needle hub 80. For example, the distal end of the needle 78 can protrude from the needle hub less than about 0.25 inches, about 0.25 inches, about 0.30 inches, about 0.35 inches, about 0.40 inches, about 0.45 inches, about 0.50 inches, about 0.55 inches, about 0.60 inches, about 0.65 inches, about 0.70 inches, about 0.75 inches, about 0.80 inches, about 0.85 inches, about 0.90 inches, about 0.95 inches, about 1 inch or greater than about 1 inch. In a further aspect, the needle 78 can be secured to the needle hub 80 by any of multiple manufacturing means such as, for example and without limitation, glue, other adhesive, or the needle hub can be molded around the needle that can have laser etched or manufactured "stops" to prevent needle slippage through the needle hub 80.

In a further aspect, and referring to FIGS. 19-22, the central bore 110 of the frusto-conical member 50 of the needle hub 80 can have a frusto-conical shape that expands outwardly, relative to a longitudinal axis of the needle hub, from proximate the proximal end 100 of the needle hub to the distal end of the needle hub. As shown, it is contemplated that the elongate needle can be mounted therein the proximal end 100 of the needle hub to be selectively placed into fluid communication with the syringe. In this aspect, the central bore 110 can further define at least two progressively increasing tapering frusto-conical shapes, 111, 113, relative to the longitudinal axis of the needle hub, which is typically aligned with the mounted needle. In one aspect, these progressively increasing tapering frusto-conical shapes can provide structural support for the needle 78 itself while allowing a desired degree of needle deflection, relative to the longitudinal axis of the needle hub for patient comfort and desired medicant application.

Figure 13:
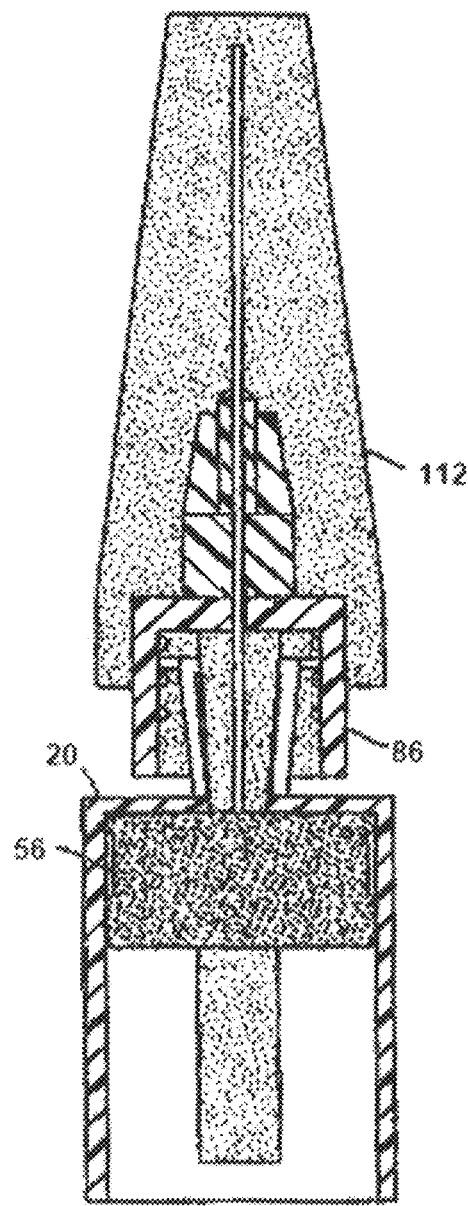
FIG. 13 is a cross-sectional view of the needle assembly of FIG. 10, showing a needle guard positioned over the needle, according to one aspect.
Figure 14:
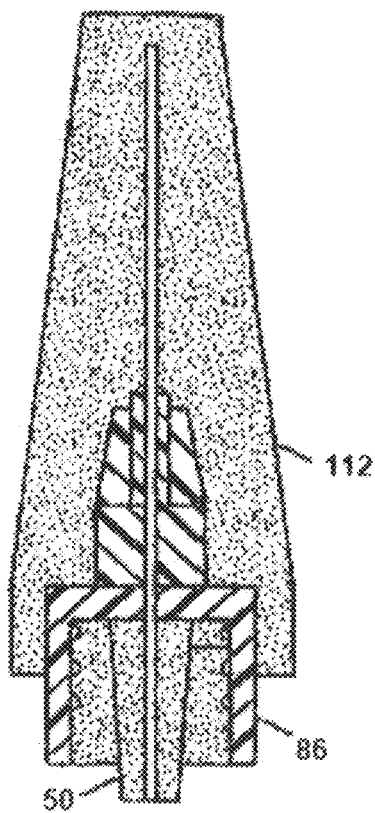
FIG. 14 is an exploded cross-sectional view of the needle assembly of FIG. 0, showing a needle guard positioned over the needle and a base guard aligned to overlap at least a portion of the a needle base, according to one aspect.
Figure 14:
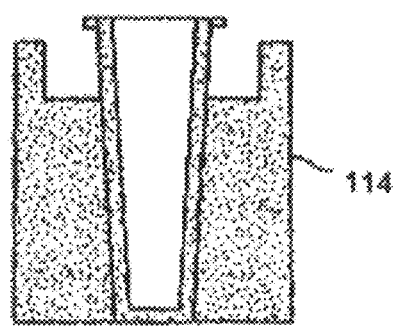
Figure 15:
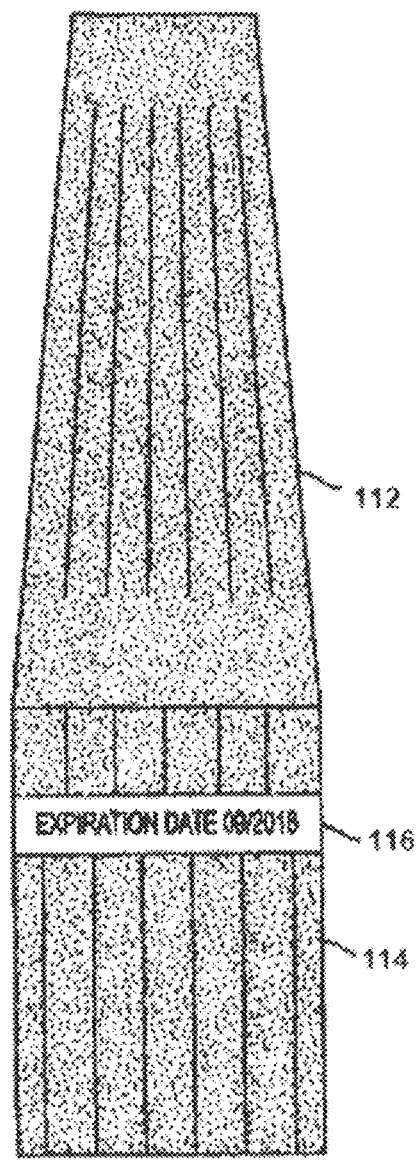
FIG. 15 is an elevational view of the needle guard and the base guard of FIG. 14, showing the guards is a closed position, according to one aspect.

As shown in FIGS. 13-15, the needle assembly 14 can further comprise at least one of a selectively removable needle guard 112 and a selectively removable base guard 114, according to one aspect. In another aspect, the needle guard 112 can be sized and shaped to cover the needle 78 and to overlap at least a portion of the needle base 86 of the needle hub 80. In a further aspect, the base guard 114 can be sized and shaped to cover the frusto-conical member 50 of the needle hub and to overlap at least a portion of the needle base. The needle guard and the base guard can be removably coupled to the needle assembly 14 by snapping to the needle assembly and/or screwing to the needle assembly 14. In still another aspect, the needle guard 112 and the base guard 114 can be sized and shaped to be substantially flush with each other when both guards are installed on the needle assembly. Optionally, the needle guard and/or the base guard can be secured to each other by a twist breakable label 116 that can have manufacturing and expiration date information and the like. When both the needle guard 112 and the base guard 114 are installed and positioned around the needle assembly (i.e., in a closed position) the needle guard and the base guard can cooperate to maintain the sterility of the needle 78 during packaging, shipment and storage.

To use the needle 78 and syringe 12 of the current application, the base guard 114 can be removed from the needle hub 80 holding the desired needle 78. For example, if medication is to be aspirated from a container, a needle hub having a 25G needle can be selected. The frusto-conical member 50 of the needle hub can be inserted into the frusto-conical void 42 of the syringe tip 40, and the needle hub 80 can be rotated approximately 180 degrees so that the flanges 52 of the syringe 12 engage the threads 88 of the needle base, thereby securing the needle hub 80 to the syringe. That is, the needle hub and the syringe can be oppositely rotated into and relative to one another. The needle hub 80 can be engaged and securely and tightly drawn into the syringe tip 40 thus removing most or all of the dead space in the interior void 42 of the syringe tip.

The user can then insert the tip of the needle 78 into a vial containing the desired fluid, and withdraw the plunger 54 to suck the fluid through the lumen 118 of the needle and into the chamber 30 of the syringe 12. The needle 78 can be changed, if desired, by reversing the rotation of the needle hub 80 relative to the syringe 12 to disengage the first needle from the syringe, and a new needle can be attached to the syringe as before. To eject the fluid from the chamber 30, the user can depress the plunger to urge the desired amount of fluid from the chamber of the syringe 12, through the aperture 44 in the end wall 20 and into the lumen 118 of the needle. If the fluid is to be ejected into a patient, the distal end 84 of the needle can pierce the skin of the patient prior to depressing the plunger 54.

As can be appreciated, the body 16 of the syringe can be marked as appropriate for the dilution level of medication in the syringe 12. As can also be appreciated, the flat surface of the distal end 72 of the piston cap 56 can be urged into contact with the end wall 20 of the body 16 of the syringe (as illustrated in FIGS. 2 and 13), thereby removing most or all of the dead space in the chamber 30 of the syringe. Furthermore, the removal of this dead space (and removal of the dead space between the interior void 42 of the syringe tip 40 and the frusto-conical member 50 of the needle hub) can remove areas in which medication could remain during and after injection, making this needle and syringe assemblage 10 efficient for a low-waste syringe 12 with interchangeable needles. The only waste with the syringe and needle of this application can be inside the lumen 118 of the needles themselves. It is also within the purview of exemplary embodiments of the present invention to include hollow bodies having syringe tips configured to accept removable or fixedly attached needles or needle hub assemblies and the like.

It is also contemplated that the syringe 12 of the present invention can be a prefilled syringe. In this aspect, the prefilled syringe 12 can be in an assembled condition, which contains a medicament or other preparation. In one aspect, the prefilled syringe 12 can be out of contact with the needle, which is typically formed from stainless steel.

In this prefilled syringe embodiment, the medicament is adapted to be contained in the chamber 30 that is defined in the hollow body 16. In this aspect, the rear end of the chamber of the hollow body is adapted to be sealed or closed by means of the piston cap 56, which can have one of a number of fittings for engagement with the plunger 54 in order to act as a piston in selectively expelling the prefilled medicant contents of the barrel. In one example, the piston cap can be formed of a self-sealing elastomer, a conventional material such as natural or synthetic rubber, and the like. The piston cap 56 can also have a plurality of concentric ribs that are defined on its outer surface for sealing engagement with the inner walls of the chamber 30 of the hollow body 16. It will be appreciated that the chamber 30 having this initially rearwardly located piston cap 56 can be aseptically filled with the selected medicament through the relatively wide mouth of the syringe tip 40 following sterilization. A needle assembly can then be aseptically assembled on the syringe tip 40.

In accordance with the present invention, the forward end of the chamber of the hollow is sealed. In one aspect, the forward end of the syringe tip 40 can be selectively sealed by a penetrable diaphragm, which is configured to effectively seal off the interior void 42 of the tip. It is contemplated that, in operation, the penetrable diaphragm can be selectively penetrated by the proximal end of a double ended needle for purposes of providing access to the interior void and, consequently, the medicant contents contained within the chamber 30.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A low waste syringe, comprising:
   a hollow body having an inner diameter, an inner wall and an end wall that closes the hollow body at a forward end of the hollow body, wherein the hollow body has an open rear end and defines a chamber;
   a piston means having a piston cap for reciprocal sealing engagement with the inner wall of the hollow body to define a chamber in the hollow body that is configured for selectively containing a fluid;
   a syringe tip mounted on the end wall of the hollow body, the syringe tip having a circumferential wall that extends along a longitudinal axis away from the hollow body of the syringe, wherein an interior surface of the circumferential wall defines an inferior void having a substantially frusto-conical shape that extends between a first end and a second end of the syringe tip, wherein an aperture is defined in the end wall of the hollow body to place the interior void in sealed fluid communication with the chamber of the hollow body, wherein the first end of the syringe tip has a first diameter configured to be coupled to the end wall of the hollow body and the second end of the syringe tip is positioned a predetermined distance from the end wall and has a second diameter that is greater than the first diameter, and wherein the second distal-end of the syringe tip further comprises at least one flange that is configured to project radially away from the second end of the syringe tip, and a needle assembly comprising an elongate needle and a needle hub that is configured to selectively matingly engage to the at least one flange of the syringe tip, wherein the needle hub comprises a needle base and a frusta-conical member, wherein the frusta-conical member has a distal end coupled to an end wall of the needle base and a proximal end that extends longitudinally outwardly a predetermined distance from the end wall of the needle base wherein the needle base of the needle hub has at least one thread configured to engage the at least one flange of the syringe tip and defines a central bore that extends through the an end wall of the needle base and the frusta-conical member, wherein the elongate needle is positioned in the central bore such that a proximal end of the needle is mounted proximate the proximal end of the frusta-conical member, and wherein, upon engagement of the needle hub to the syringe tip via the operative engagement of the thread tread of the needle base and the at least one flange, the entire exterior surface of the frusto-conical member of the needle hub base is configured to slideably engage the entire interior surface of the syringe tip and the aperture of the hollow body such that the frusto-conical member of the needle base fills the interior void of the syringe tip and the aperture of the hollow body to form a fluid tight seal and to minimize any dead space in the low waste syringe.

2. The low waste syringe of claim 1, wherein the body of the syringe has a length of less than about 7.0 cm.

3. The low waste syringe of claim 1, wherein the body of the syringe has a length of greater than about 10.0 cm.

4. The low waste syringe of claim 1, wherein the body of the syringe has a length between about 7.0 cm to about 10.0 cm.

5. The low waste syringe of claim 1, wherein the outer diameter of the body of the syringe is less than about 0.25 cm.

6. The low waste syringe of claim 1, wherein the outer diameter of the body of the syringe is greater than about 2.0 cm.

7. The low waste syringe of claim 1, wherein the outer diameter of the body of the syringe is between about 0.25 cm to about 2.0 cm.

8. The low waste syringe of claim 1, wherein the outer diameter of the body of the syringe is substantially constant.

9. The low waste syringe of claim 1, wherein the inner diameter of the body of the syringe varies the volume capacity of the chamber of the body.

10. The low waste syringe of claim 1, further comprising a plurality of longitudinally extending hatch marks positioned on an outer wall of the body to indicate the amount of fluid contained in the chamber.

11. The low waste syringe of claim 10, wherein the hatch marks indicate concentration of fluid contained in the chamber of the syringe.

12. The low waste syringe of claim 10, wherein the hatch marks indicate d volume of a medication per volume of a diluent.

13. The low waste syringe of claim 10, wherein the hatch marks indicate relative units of a medication per volume of a diluent.

14. The low waste syringe of claim 13, wherein the hatch marks indicate relative units of neurotoxin per volume of diluent.

15. The low waste syringe of claim 1, wherein the needle assembly comprises at least one interchangeable needle assembly.

16. The low waste syringe of claim 1, wherein the syringe tip has a substantially cylindrical outer surface shape.

17. The low waste syringe of claim 1, wherein the piston means further comprising a plunger coupled to the piston cap.

18. The low waste syringe of claim 17, wherein a distal end of the piston cap is configured to complementarily engage the end wall of the body of the syringe.

19. The low waste syringe of claim 18, wherein the distal end of the piston cap is sized and shaped so that, in a depressed position, in which the distal end of the piston cap contacts the end wall, there are substantially no gaps formed between the end wall and the distal end of the piston cap.

20. The low waste syringe of claim 1, wherein the needle base has a cylindrical hollow shape, and wherein the frusto-conical member is formed in the needle base of the needle hub.

21. The low waste syringe of claim 20, wherein the proximal end of the frusto-conical member of the needle hub extends longitudinally outwardly beyond the needle base.

22. The low waste syringe of claim 1, wherein the central bore has a frusto-conical shape that expands outwardly, relative to a longitudinal axis of the needle assembly, from proximate a proximal end of the needle hub to the distal end of the needle hub.

23. The low waste syringe of claim 1, wherein the central bore defines at least two progressively increasing tapering frusta-conical shapes, relative the longitudinal axis of the needle hub.

24. The low-waste syringe of claim 1, wherein the chamber is prefilled with a medicant.

25. A low waste syringe, comprising:
a hollow body having an inner diameter, an inner wall and an end wall that closes the hollow body at a forward end of the hollow body, wherein the hollow body has an open rear end and defines a chamber;
a piston means having a piston cap for reciprocal sealing engagement with the inner wall of the hollow body to define a chamber in the hollow body that is prefilled with a fluid medicant;
a syringe tip mounted on the end wall of the hollow body, the syringe tip having a circumferential wall that extends along a longitudinal axis away from the hollow body of the syringe, wherein an interior surface of the circumferential wall defines an interior void having a substantially frusto-conical shape that extends between a first end and a second end of the syringe tip, wherein an aperture is defined in the end wall of the hollow body to place the interior void of the syringe tip in sealed fluid communication with the chamber of the hollow body, wherein the first end of the syringe tip has a first diameter configured to be coupled to the end wall of the hollow body and the second end of the syringe tip is positioned a predetermined distance from the end wall and has a second diameter that is greater than the first diameter, wherein the interior surface defined in the syringe tip defines a substantially frusto-conical shaped void extending between the respective first and second ends of the syringe tip, and wherein the second end of the syringe tip further comprises a pair of flanges positioned in opposition, each flange being configured to project radially away from the second end of the syringe tip; and
a needle assembly comprising an elongate needle and a needle hub that is configured to selectively matingly engage to the pair of flanges of the syringe tip, wherein the needle hub comprises a needle base and a frusto-conical member, wherein the frusto-conical member has a distal end coupled to an end wall of the needle base and a proximal end that extends longitudinally outwardly a predetermined distance from the end wall of the needle, wherein the needle base of the needle hub has at least one thread configured to engage the pair of flanges of the syringe tip and defines a central bore that extends through the end wall of the needle base and the frusto-conical member, wherein the elongate needle is positioned in the central bore such that a proximal end of the needle is mounted substantially aligned with the proximal end of the frusto-conical member, and wherein, upon engagement of the needle hub to the syringe tip via the operative engagement of the thread of the needle base and the pair of flanges, the entire exterior surface of the frusto-conical member of the needle hub is configured to slideably engage the entire interior surface of the syringe tip and the aperture of the hollow body such that the frusto-conical member of the needle base fills the interior void of the syringe tip and the aperture of the hollow body to form a fluid tight seal and to minimize any dead space in the low waste syringe.

26. The low waste syringe of claim 25, wherein a distal end of the piston cap is configured to complementarily engage the end wall of the body of the syringe.

27. The low waste syringe of claim 26, wherein the distal end of the piston cap is sized and shaped so that, in a depressed position, in which the distal end of the piston cap contacts the end wall, there are substantially no gaps formed between the end wall and the distal end of the piston cap.

* * * * *